United States Patent [19]
Artinian

[11] Patent Number: 5,632,298
[45] Date of Patent: May 27, 1997

[54] RESUSCITATION AND INHALATION DEVICE

[76] Inventor: Hagop Artinian, 81 Mack Avenue, Scarborough, Ontario, Canada, M1L 1M8

[21] Appl. No.: 405,957

[22] Filed: Mar. 17, 1995

[51] Int. Cl.$^6$ ................................................. A61M 16/00
[52] U.S. Cl. ................ 137/102; 128/204.19; 137/493.2; 137/512.2; 137/599; 137/908; 251/65
[58] Field of Search ................ 137/102, 908, 137/599, 512.2, 493.2; 251/65; 128/204.19, 205.24

[56] References Cited

U.S. PATENT DOCUMENTS

| | | | |
|---|---|---|---|
| 2,865,531 | 12/1958 | Gorst et al. | 137/493.2 X |
| 3,459,216 | 8/1969 | Bloom et al. | 137/512.2 X |
| 3,515,163 | 6/1970 | Freeman | 137/102 |
| 4,121,580 | 10/1978 | Fabish | 137/102 X |
| 5,230,330 | 7/1993 | Price | 128/203.11 |
| 5,398,714 | 3/1995 | Price | 137/102 |

Primary Examiner—Stephen M. Hepperle
Attorney, Agent, or Firm—Paul Sharpe; McFadden, Fincham

[57] ABSTRACT

A resuscitation and inhalation device which can be used alternatively in each of two modes. The flow of oxygen or gas is controlled by a control valve, itself controlled by a movable member acted upon by the pressure of oxygen or gas in a chamber after having flowed passed the control valve. On meeting a preset maximum pressure, the valve member moves to close the control valve. The movable valve member is acted upon by a magnetic field which is adjustable, and the magnetic field strength sets the pressure at which the valve member moves. Oxygen or gas is admitted to the control valve by two alternative inlet valves, one for resuscitation with only oxygen or gas flowing through the mask, and one for inhalation, with oxygen or gas and air or a second gas being fed through the mask, allowing ambient air to mix prior to the flow to the patient as a result of inhalation effort by the patient.

16 Claims, 8 Drawing Sheets

RESUSCITATION AND INHALATION DEVICE

FIELD OF THE INVENTION

This invention relates to a flow control valve device.

BACKGROUND OF THE INVENTION

More particularly, one aspect of this invention relates to a flow control valve for use in devices for controlling a source of fluid. Inasmuch as the present invention has particular application as a flow control valve for equipment such as inhalation devices, particular reference will be made to such devices in describing the present invention, although it is understood that the flow control valve may be used for various purposes, such as those described hereinafter.

Masks for resuscitation, where oxygen or gas is fed to a person for breathing and for inhalation, are known where a mixture of oxygen or gas and air or other gas is fed to a person, or primarily used by non-medical personnel, such as firefighters, police and ambulance personnel. Information concerning the person being treated is usually not available. Therefore, great care and attention is required to prevent a mishap from occurring, particularly in relation to the person being treated. The oxygen or gas, which is supplied to the lungs of the person, is usually supplied in containers of a relatively high pressure.

The other option which is available for resuscitation is directed to the use of a simple flexible container and mask for fitting over the nostrils and mouth of a patient. In use, the flexible container is simply squeezed by an operator to discharge the predetermined volume of gas from the container into the lungs of the patient. This apparatus is inherently limited by its simplistic nature and has limited utility where blood gas content is important based on inspiration and expiration rates. Where the inspiration and expiration rates are to be controlled, this apparatus clearly has limited utility.

In view of what is currently available for resuscitation and inhalation devices, it is clear that a need exists for an improved arrangement where the operator can select and monitor the pressure during inspiration and the flow during expiration as well as varying the pressure and frequency during these two phases of the ventilatory cycle.

SUMMARY OF THE INVENTION

One object of the present invention is to provide an improved resuscitation and inhalation device.

The present invention provides a resuscitation and inhalation device, suitable for manual or automatic operation by medical or non-medical persons. Safeguards are provided to ensure that safe maximum pressures will not be exceeded. Oxygen or gas under a selected maximum pressure enters on operation of an inlet valve, the oxygen or gas flowing passed a first open valve into a chamber. The oxygen or gas in the chamber acts on a movable valve member which, when the oxygen or gas pressure in the chamber reaches the preset maximum pressure, moves against a magnetic field, permitting the first valve to close. Oxygen or gas flows from the chamber through connections to a face mask. The lungs are inflated at this time and then the patient starts to exhale. The patient's breath passes the movable valve member to escape. At the conclusion of the exhaling step, the movable valve member moves under light spring pressure to open the first valve. The initial pressure of the movable valve member is set by the strength of the magnetic field experienced by the movable valve member, the magnetic field being adjustable. Flow of oxygen or gas will continue as long as the inlet valve is held open, to provide resuscitation.

For inhalation, where a mixture of oxygen or gas and air or a different gas is continuously supplied, and inhaled by the patient, a second valve is activated to allow a continuous feed of oxygen or gas. By connections, the oxygen or gas again flows passed the first, open valve to the chamber. The same control of maximum oxygen or gas pressure occurs by the movable valve member. The oxygen or gas then flows to a mixing chamber, where it mixes with air or a different gas and then flows to the face mask.

In the prior art, there are numerous references which describe flow control valves. For example, reference may be made to the following United States patents, namely, Schreiber et al. U.S. Pat. No. 3,039,481 (1962);

U.S. Pat. No. 3,209,748—Thomas (1965);
U.S. Pat. No. 4,606,339—Walther (1986);
U.S. Pat. No. 4,664,355—Kubach (1987);
U.S. Pat. No. 4,796,619—Walther (1989);
U.S. Pat. No. 4,825,904—Grau et al. (1989);
U.S. Pat. No. 402,779—Steinhoff (1889);
U.S. Pat. No. 2,364,626—Emerson (1944);
U.S. Pat. No. 3,279,487—Elam (1966);
U.S. Pat. No. 3,333,581—Robinson et al. (1967);
U.S. Pat. No. 3,509,899—Hewson (1970);
U.S. Pat. No. 3,610,237—Barkalow et al. (1971);
U.S. Pat. No. 4,297,999—Kittell (1981); and
U.S. Pat. No. 4,349,015—Alferness (1982).

The above references teach valves which generally tend to include very complex components or alternatively, have limited application due to their structural features. Some of these references do disclose the use of magnetic valves, e.g., U.S. Pat. No. 4,664,355—Kubach (1987), as well as U.S. Pat. No. 4,796,619—Walther (1989), the latter permitting sourcing of a single incoming gaseous fluid.

There is a need for a relatively simple, reliable and economical device which can be used in different functional modes, and to this end, one aspect of the present invention includes the feature that energy required to change the valve states is derived from the magnetic property of the valve with minor assist using a component associated with the magnetic valve, and operating in conjunction with the pressures in a variable pressure system.

One of the primary objects of one embodiment of the present invention is to provide a flow control valve apparatus, comprising: a chamber; selective metering means in the chamber for selectively metering gas pressure in the chamber; an adjustable valve member reciprocally mounted in the chamber and act upon by gas pressure in the chamber; a flow control valve, acted upon by the valve member to an open position; means for connecting a high pressure source to an inlet of the flow control valve; means for connecting a variable pressure volume to the chamber; means for selectively connecting a low pressure volume to the chamber; a first magnetic member on the valve member; a second magnetic member in spaced opposition to the first magnetic member; one of the first and second magnetic members being magnetized, to restrain movement of the valve member by the gas pressure in the chamber; the valve member being moved against restraint when the variable pressure reaches a predetermined maximum value, to permit closing of the flow control valve, and to permit the connection of the low pressure volume to the chamber; and the valve member being moved with restraint when the variable pressure reaches a predetermined low value to open said flow control valve.

A further object of the present invention is to provide a resuscitation and inhalation apparatus including a chamber; a valve member reciprocally mounted in said chamber and acted upon by gas pressure in said chamber; a flow control valve acted upon by said valve member to an open position; means for connecting a gas volume to said apparatus, the improvement comprising:

metering means in said chamber for selectively metering gas pressure in said chamber.

In preferred embodiments, the valve member includes a plurality of components and permits adjustment of the head of the valve relative to the stem. This permits the distance between the magnetic members to be varied.

In a further advantageous feature of the present invention, the valve head may include a plurality of apertures therethrough for permitting the ingress of ambient air from outside the resuscitator to the interior of the chamber to therefor provide a mixture of gases within the chamber. Further still, a particularly attractive feature according to the present invention is the use of a one-way or directional valve which is associated with the head of the valve and is used to permit additional selective passage of air through the apertures as set forth hereinabove.

A further advantageous feature of the present invention includes an annular magnetic member in the housing, aligned with and spaced from the movable valve member, and having a flow control valve mounted for axial movement in the annular magnet.

Conveniently the device has a first oxygen or gaseous inlet valve which includes an operating member, and the operating member comprises mounting means, e.g., a button, slidable axially in a valve seating member, the first inlet valve comprising a ball valve and the mounting means or button including an extension for lifting the ball valve off its seating on movement of the button, and biasing means biasing the button to a nonoperative position. In this structure, preferably the second inlet valve comprises a needle-valve.

In order to facilitate hands free operation, the button may be provided with a cam groove for releasably locking the button in an inward position and therefor maintaining the ball valve off of its seating.

According to a preferred feature of the above structure, the device has a gaseous flow control valve which includes a stem and a head, the movable valve member acting on an end of the stem, and the head forming a seating at an end remote from the movable valve member.

The above device preferably includes an inset or insert in the annular magnet, the stem being movable axially in the inset or insert, and flats on the stem extending the length thereof, for flow of a gas passed the stem.

The device advantageously includes an inlet for supply of the gas to the alternate first and second gaseous inlet valves, and a control valve is mounted on the inlet for controlling gas flow therethrough, the control valve including a first flow passage open at all times for a predetermined minimum gas flow, and a second, openable flow passage for additional flow of gas to a predetermined maximum.

The flow control device of the present invention can be housed in an appropriate housing of suitable material; for example, a housing of plastic or non-magnetic metallic material can be utilized. Preferably, and particularly when using the flow control valve of the present invention in a resuscitation and inhalation device, the housing will be substantially airtight and dustproof to prevent undesired particulate material from gaining access to the flow control valve.

In use in an inhalation device, the device of the present invention can be provided with appropriate connections to a source of gaseous fluid such as oxygen or any other desired gas; thus, the device of the present invention is adaptable to conventional masks through appropriate conduit connections.

One of the primary features of the present invention is directed to the use of a metering system for selectively metering the flow rate of gas within the chamber to the exterior of the device. In connection with this feature, a series of grooves which preferably vary in length and may vary in depth are provided to allow a user to predetermine the rate of discharge or ingress of gas pressure within the chamber. By providing a series of grooves of varying length, some or all of the grooves may be used at any one time in order to permit gas pressure alteration within the chamber. This is a marked advantage over previously known arrangements where the operator had no control over the expiration rates of the patient during the ventilatory cycle. As is known to those skilled in the medical field, the absence of expiration or inhalation control can lead to difficulties in a situation where ventilatory parameters affecting blood gas concentration in the patient is a primary concern.

In preferred embodiments, the magnetic member is permanently magnetized—i.e., a permanent magnet, although it will be understood that for various applications, an electromagnet can be utilized with appropriate current sources.

The device of the present invention permits adjustability of the gaseous flows and pressures, and comparing the device of the present invention to prior art devices which utilize springs for adjustment, the magnetic valve arrangement permits very specific and delicate adjustments when required. Thus, the device of the present invention will find use in various types of safety valves which require precise adjustments for exact control of gaseous flows and pressures.

A primary safety feature of the present invention is that the valve releases under conditions where comparable spring-type valves would maintain pressure. Still further, the valves of the present invention are position-independent, compared to prior art systems.

Other possible applications for the control valve of the present invention include use in clutch drives, permitting compensation for wear on a clutch plate, or in heat-activated systems where complete release under the operating environment is required.

Having thus generally described the invention, reference will now be made to the accompanying drawings, illustrating preferred embodiments.

BRIEF DESCRIPTION OF THE DRAWINGS

Similar numerals in the drawings denote similar elements.

DETAILED DESCRIPTION OF THE PREFERRED EMBODIMENTS

Figure 1:
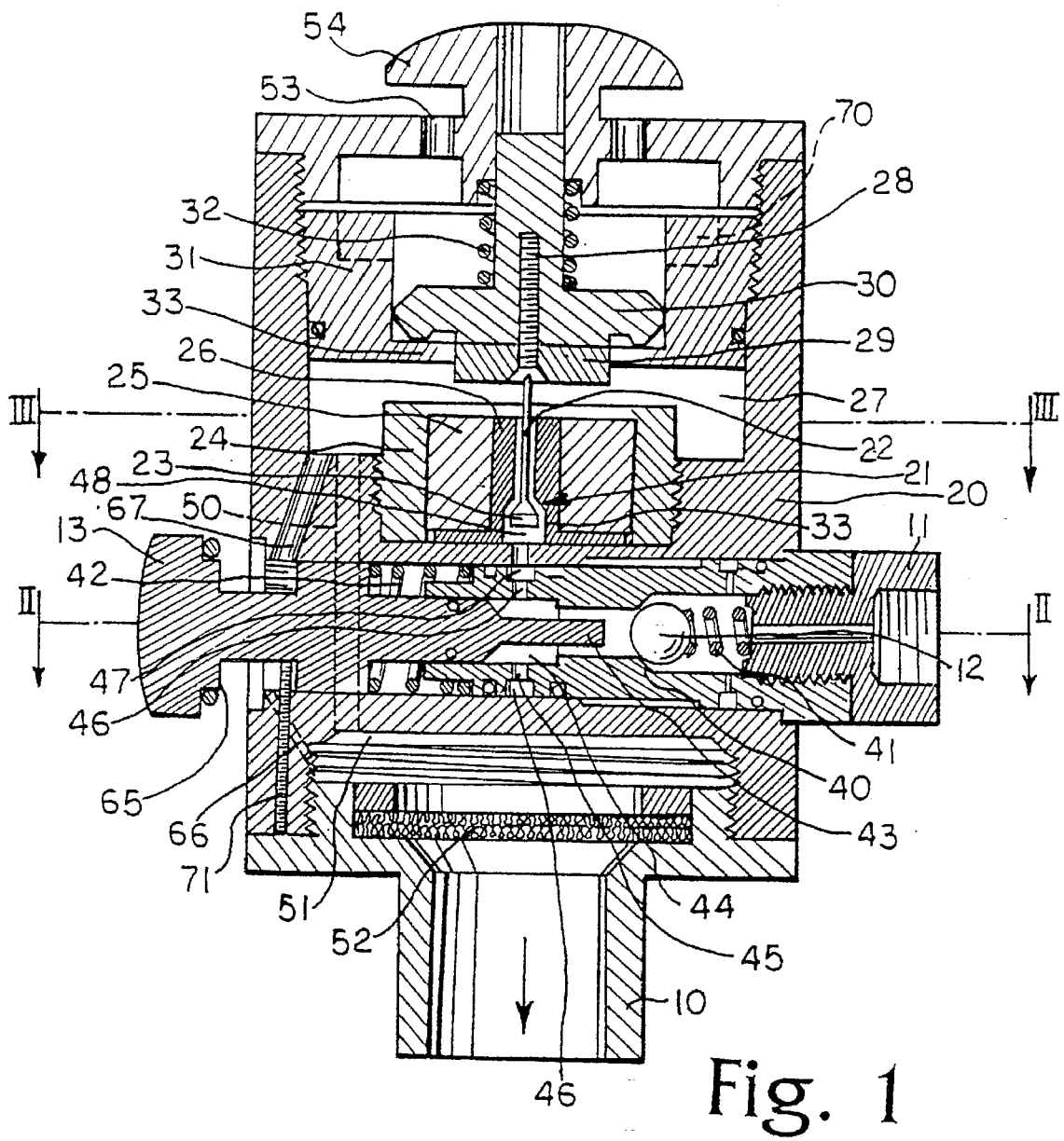
FIG. 1 is a vertical cross-section through a device of the present invention.
Figure 2:
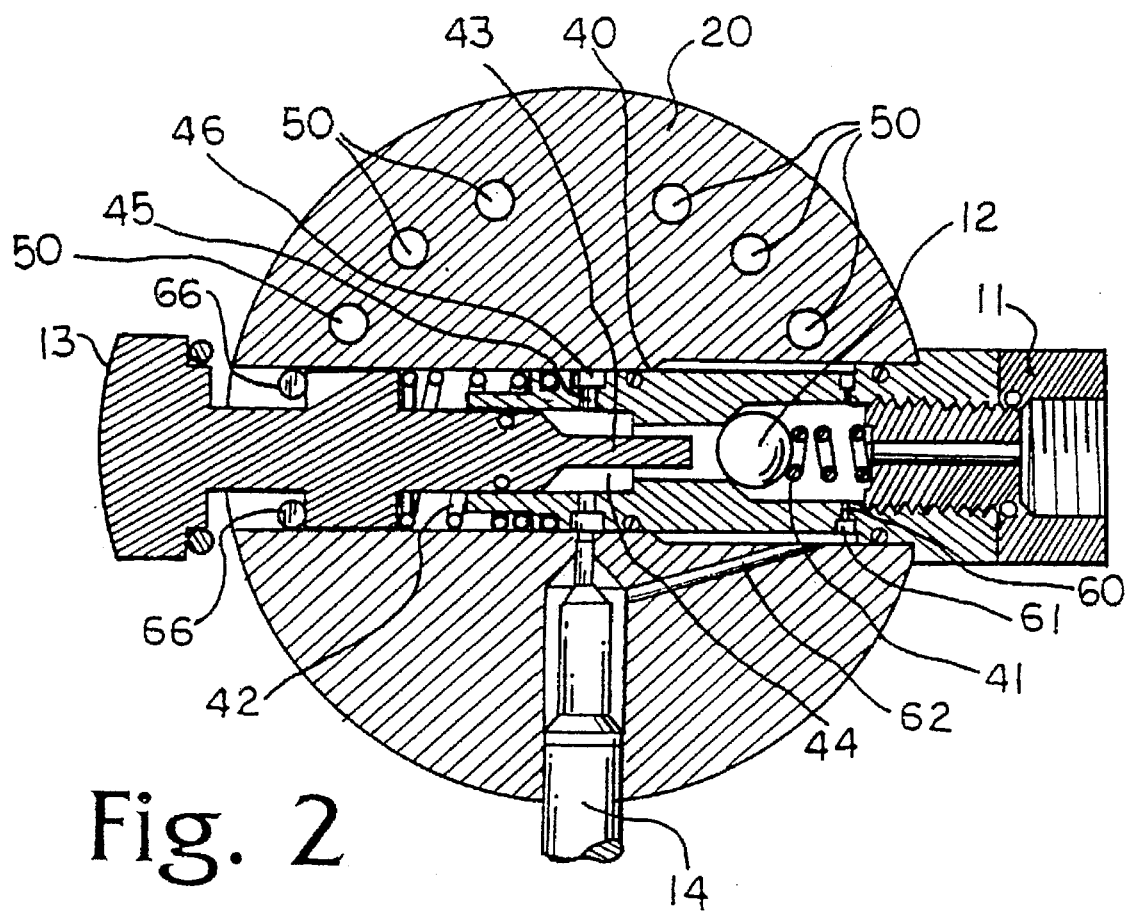
FIG. 2 is a cross-section on the line II—II of FIG. 1.
Figure 3:
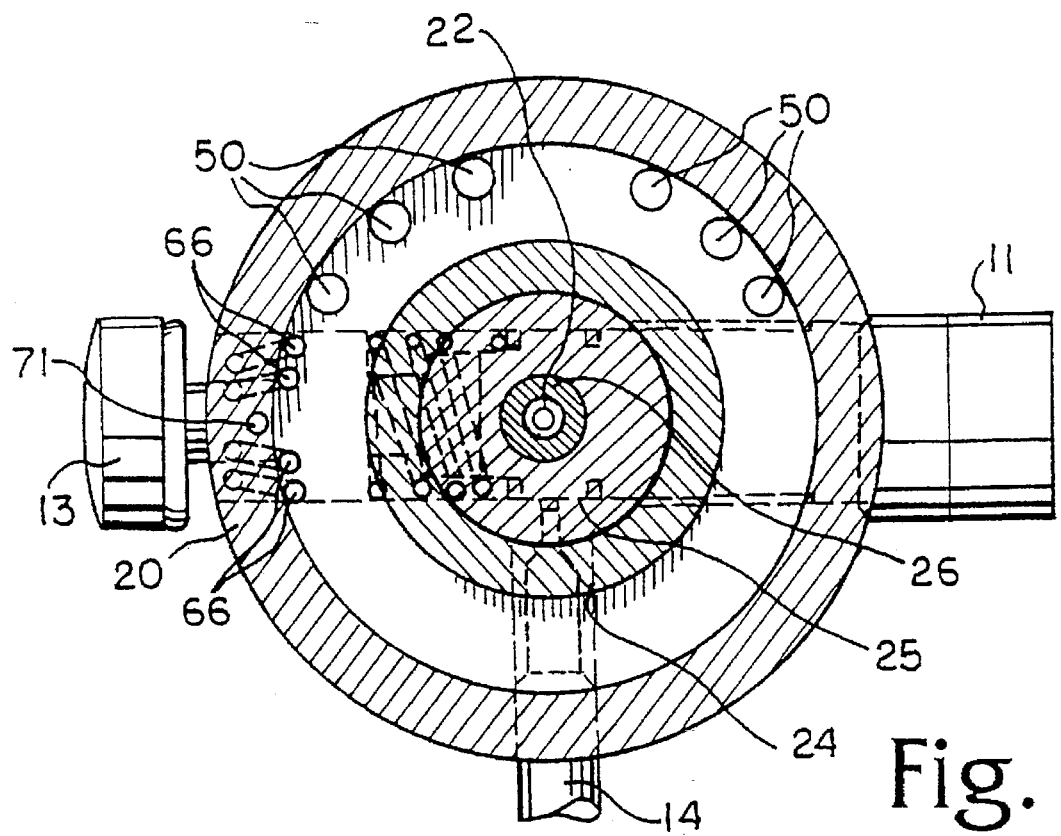
FIG. 3 is a cross-section on the line III—III of FIG. 1.

The apparatus, as illustrated in FIGS. 1, 2 and 3, is adapted to be mounted onto a conventional face mask (not shown), there being a connector 10 which connects by suitable means to the interior of the mask or exterior of the tube connection. Oxygen or gas is supplied to the apparatus at a connection 11. A first oxygen inlet valve 12, which may be a ball valve, is actuated by a button 13; and a second inlet valve 14, preferably in the form of a needle-type valve, can provide for a continuous flow of oxygen.

The apparatus comprises a main housing 20, in which is mounted an oxygen flow control valve 21, having a stem 22 and a head 23. In the example illustrated, the stem 22 has a somewhat triangular cross-section, with flats extending the length of the stem, so as to permit gaseous flow passed the stem 22. A Teflon (trade mark) member 24 holds an annular magnetic member 25, the valve stem 22 moving in an insert, for example, a Teflon insert 26. The head 23 forms a seating member for the valve 21. Surrounding the member 24 is a chamber 27. Positioned in alignment with the valve 21 is a valve member 30, for example, of Teflon, with a magnetic metal member 29 attached thereto by a bolt 28. The valve member 30 moves in an adjustable seating member 31 which can be moved axially by rotation in the housing 20 to preset the distance between the magnetic metal member 29 and the magnetic member 25. A light spring 32 biases the valve member 30 down into contact with the seating 33 of the seating member 31. In an alternative arrangement, the bore of the insert 26 can have grooves extending along the bore, the stem 22 being cylindrical.

The button 13 slides in a valve seating member 40 in which seats the valve 12, the valve 12 being biased against the seating 40 by a spring 41. The button 13 is biased to an outward position by a spring 42. The button 13 is limited in its movement by the effect on spring 42 by pin 71.

Figure 4:
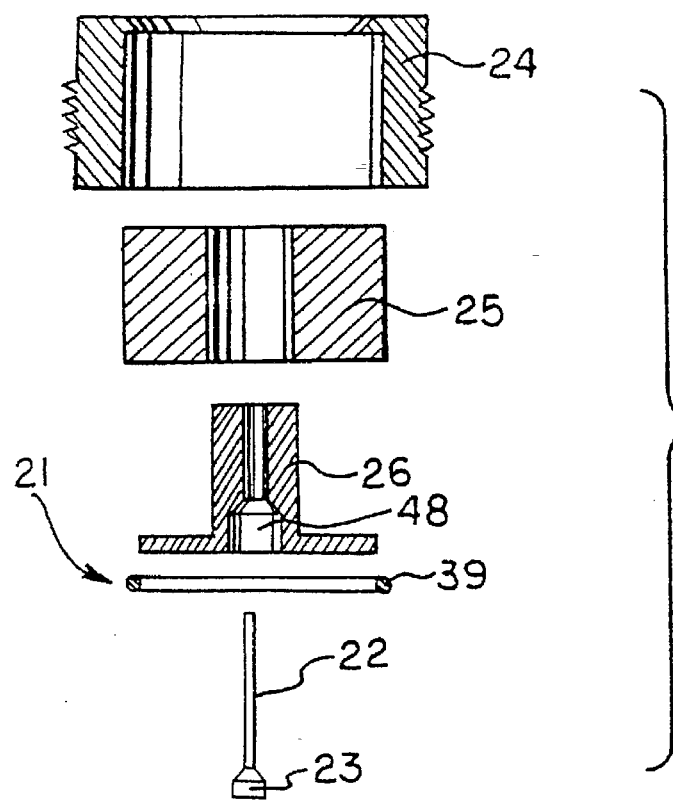
FIG. 4 is an exploded cross-sectional view of the oxygen control flow valve, magnetic member and insert, as illustrated in FIG. 1.

FIG. 3 illustrates the flow control valve 21 in more detail, showing the stem 22 and head 23, together with the annular magnetic member 25, insert 26 and the member 24, which holds the magnetic member 25 and insert 26 in position in the housing 20. Seen more clearly in FIG. 4 is an o-ring 39, which seals the insert 26 and magnetic member 25 against the housing 20.

For resuscitation, the button 13 is pushed in, with a stem 43 at the inner end lifting valve 12 off its seating 40. Oxygen flows through connection 11, past the valve 12, into chamber 44 and by passageway 45 and groove 46 and passageway 47 into the chamber 48 beneath the valve head 23 of the valve 21. With the valve 21 open, oxygen flows up past the stem 22 to the chamber 27. From the chamber 27, the oxygen flows through passageways 50, chamber 51, through filter 52 into the connector 10 and then to the face mask.

The oxygen in the chamber 27 acts on the lower end of the valve member 30, and when the pressure in the chamber 27 reaches the maximum desired pressure, the valve member 30 moves up and allows valve 21 to close. The valve 21 closes under the action of the flow of oxygen from passageway 47. This will represent the end of the inhalation phase of the patient. The patient then exhales, via the chamber 51, passageways 50, chamber 27, passed valve 30 via recesses 70, and out of vents 53, the air being deflected by deflector 54. When the patient stops exhaling, valve member 30 is returned by spring 32, valve 21 is open and the sequence restarts. The pressure at which the valve member will start to move will depend upon the magnetic effect of the magnet 25 on the magnetic metal member 29. This can be determined by varying the distance between magnet 25 and magnetic metal member 29, and this obtained by the adjustable seating member 31.

Figure 1A:
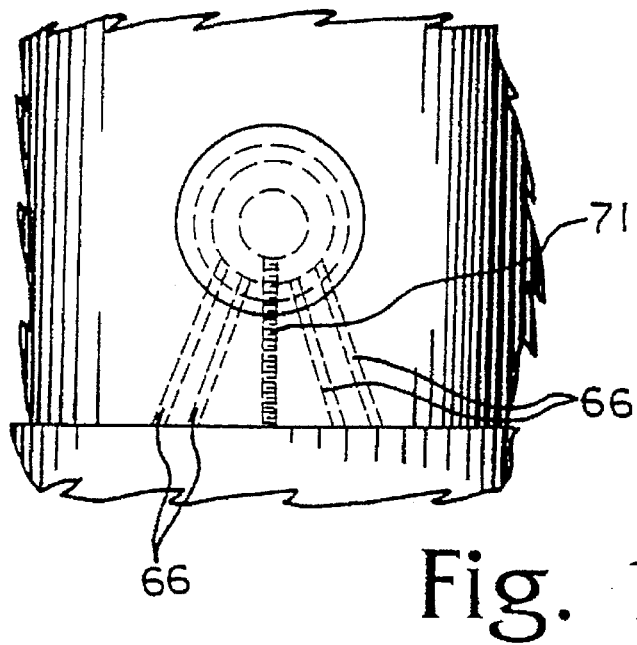
FIG. 1A is a partial side view, in the direction of the arrow A in FIG. 1, with the button head 13 omitted for clarity.

For inhalation, a controllable continuous flow of oxygen is provided by the valve 14. Oxygen flows from connector 11 through grooves 60 and 61, passageway 62, past the valve seating member 40 and into the groove 46 through passageway 47 to the chamber 48. It then flows up past valve 21, into chamber 27, and through passageways 50 to chamber 51. In the resuscitation mode, when the button 13 is pushed in, an annular seat 65 shuts off access to passageways 66, which otherwise permits air to enter chamber 51, and in addition, access to passageway 67 is cut off. In the inhalation mode, the button 13 is in an outer position, thus air flows into chamber 51 to mix with the oxygen and flow to the connector 10, and also flows into the chamber 27. The passageways 66 are seen more clearly in FIG. 1A and are also see in FIG. 3.

The valve member 30 acts in the same manner to control the maximum oxygen pressure in chamber 27. On reaching the desired maximum pressure, i.e., at the end of inhalation, the valve 30 moves, thereby closing valve 21. At the end of exhalation, the valve member 30 opens valve 21 for the sequence to resume. The exhaled breath passes through the chamber 51 and out the passageway 67.

Figure 5:
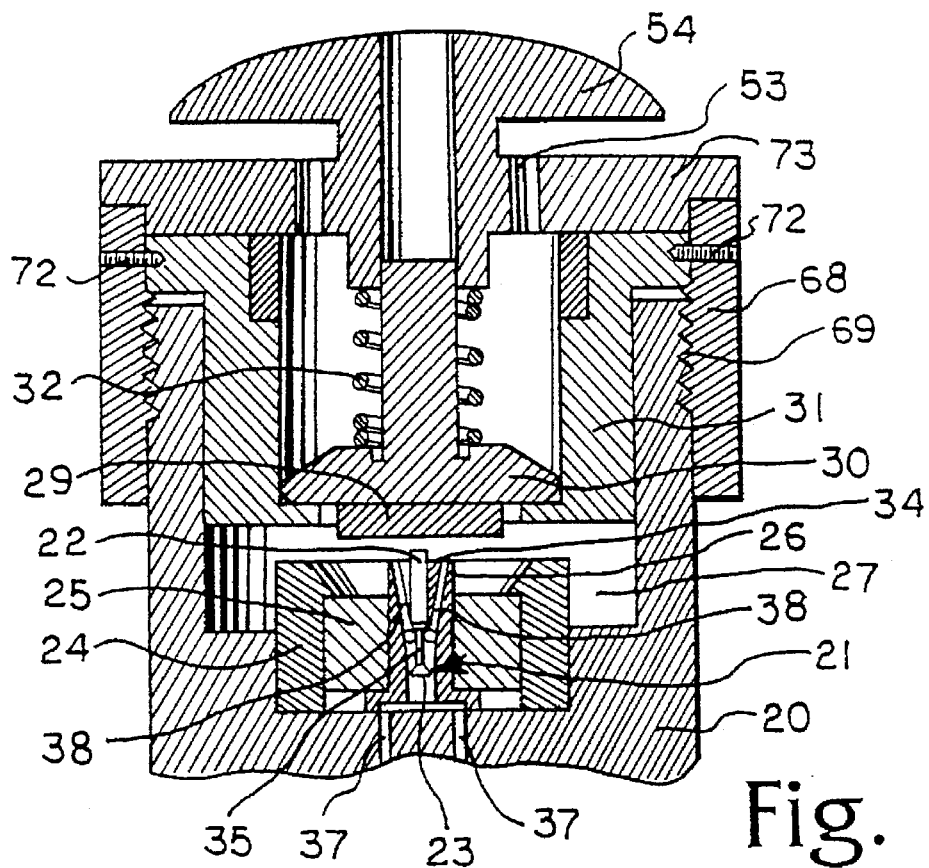
FIG. 5 is a cross-section similar to that of FIG. 1, but of the upper part of the device only, illustrating a modification thereto.

In the arrangement illustrated in FIG. 5, in which reference numerals common with FIG. 2 are used where applicable, the adjustment of the seating member 31 is obtained by an exterior sleeve 68 rotationally connected to the housing 20 via the screw thread 71, and fixedly connected to the seating member 31, via screws 72. Rotation of the sleeve 68 relative to the housing 20 will move the sleeve up or down, depending upon the direction of rotation. The seating member 31, with the cap 73 and deflector 54, will move with the sleeve 68 as a unit. Movement of the seating member 31 will vary the distance, and thus the magnetic attraction, between magnet 25 and the member 29.

Also illustrated in FIG. 5 is a modification to the flow control valve 21. The valve stem 22 preferably has a circular cross-section, reciprocal in a bore 34 in the insert 26, and is relatively closely fitted in the bore 34, but freely slidable therein. The stem 22 has a reduced cross-section 35 just above the head 23, and the head seats against an O-ring 39 positioned in an enlarged portion of the bore 34. The lower end of the insert 26 has an annular recess or chamber 48. Instead of a single passageway 47 in the housing 20 as in FIG. 1, two bores 37 are provided, spaced apart and opening into the recess 36. Further bores 38 extend up from the bore 34 behind the O-ring 39 into the chamber 27. When the valve 21 is opened, flow occurs through the two bores 37, passed the head 23 and O-ring 39, and through the bores 38 into chamber 27. The valve stem 22 is guided in the bore 34. The number of bores 38 can vary, for example, three or more. The provision of the two bores 37 is to avoid any possible "jet" action through a single bore or similar passage holding the valve 21 shut.

Figure 6:
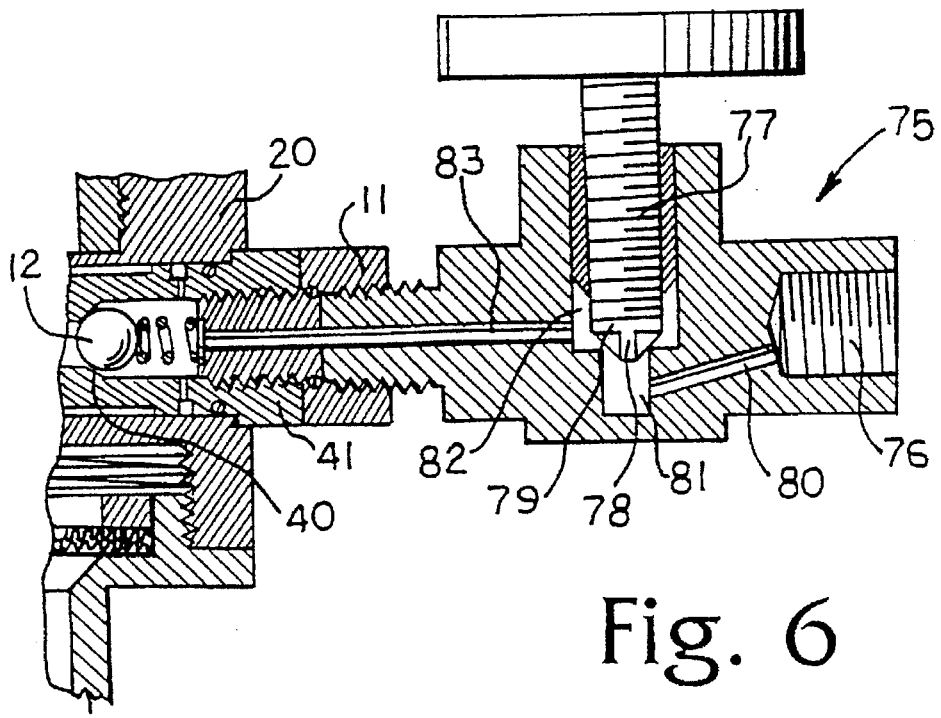
FIG. 6 shows the application of a flow control valve to the main oxygen connection to the device.

For safety and other reasons, the supply of oxygen can be via a control valve which permits a predetermined minimum flow at all times. FIG. 6 illustrates such a valve, indicated generally at 75, connected to the oxygen connection 11, the oxygen supply being connected to the valve 75 at inlet 76. The valve control member 77 has a central bore 78 at its lower end, with a cross-bore 79 spaced above the seating position of the control member 77. Bore 80 connects inlet 76 to a chamber 81 below the valve control member 77. When closed, the control member 77 seats on the upper periphery of the chamber 81, but a minimum flow still occurs through bores 78 and 79 to chamber 82 and thence via a bore 83 to the first valve 12 (see FIGS. 1, 2 and 6). The bores 78 and 79 control the minimum flow. When the valve 12 is opened by operation of the control member 77, increased flow is obtained between the bottom or seat of the control member 77 and the upper periphery of the chamber 81. The maximum flow obtainable can be set by the diameter of the bore 83. The valve 75 controls the minimum flow of oxygen available at all times to the device and also the maximum flow which can be provided to the device. The various valves in the device actually control the flow of oxygen to the user. As an example, the minimum flow can be 40 liters per minute and the maximum flow, 90 liters per minute.

Figure 7:
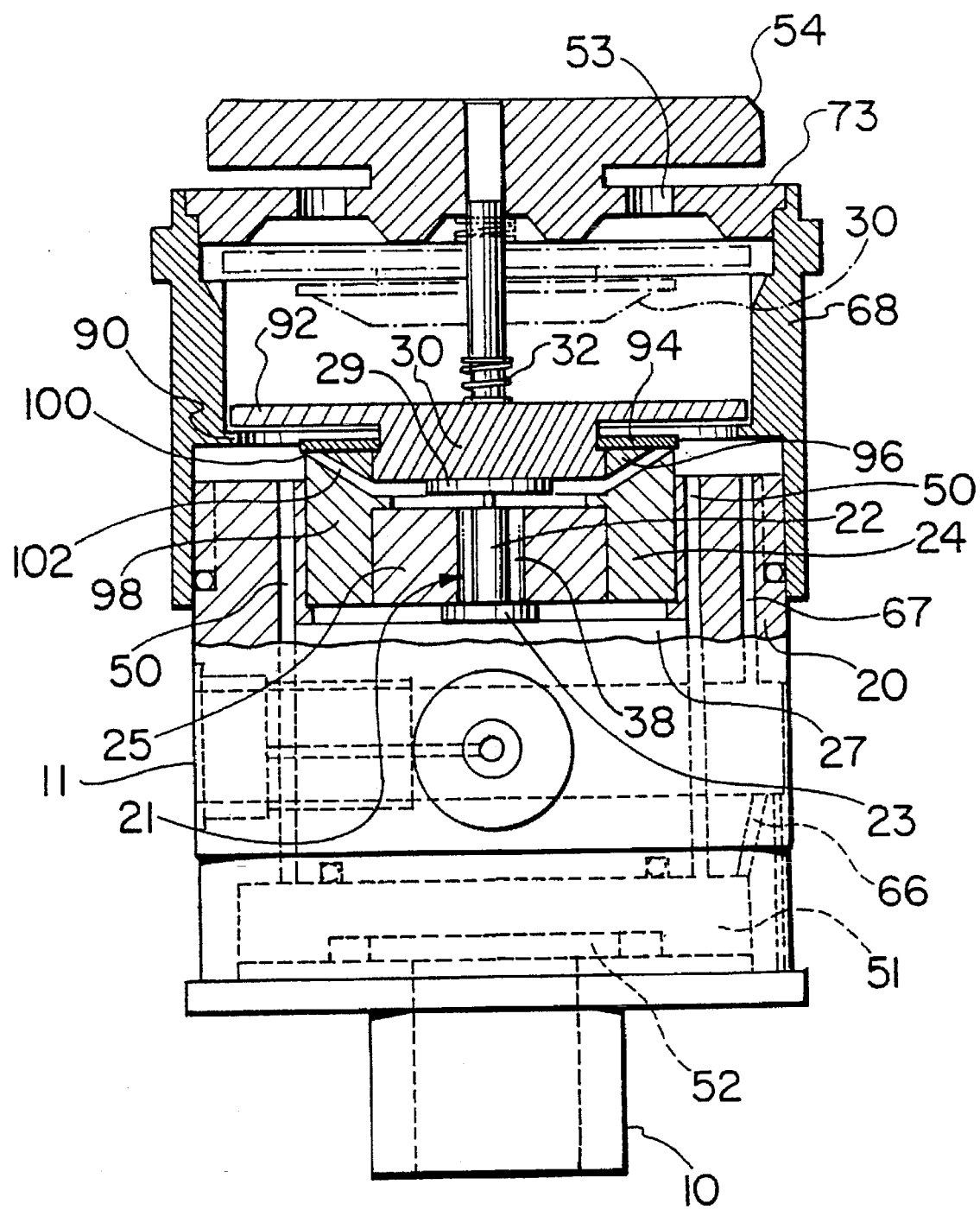
FIG. 7 is a cross-section of the upper part of the device as in FIG. 5 illustrating further modifications.

FIG. 7 illustrates a further modification, in which the action of a valve 30 is modified. Where applicable common reference numerals are used. In this embodiment, the sleeve 68 embodies the seating member 31 of FIG. 1 and 5, in that an annular flange 90 extends radially inward from the bore of the sleeve 68 and forms a seating member. Resting on the flange 90 is an annular valve member 92. As the valve 30 moves upward in FIG. 7, the valve 92 lifts off the flange 90.

The valve member 30 is modified to carry below the main valve portion an annular flap valve member 94. This flap valve is retained on the valve member 30 by an annular member 96 and can move a small distance axially.

The Teflon member 24 is modified by having an upwardly extending rim 98 forming an annular seating 100. The rim 98 has a downwardly and inwardly extending inner surface 102. In its downward position, the flapper valve 94 seals on the annular seating 100 of the rim 98. This initially prevents the valve member 92 seating on the flange 90.

Figure 8:
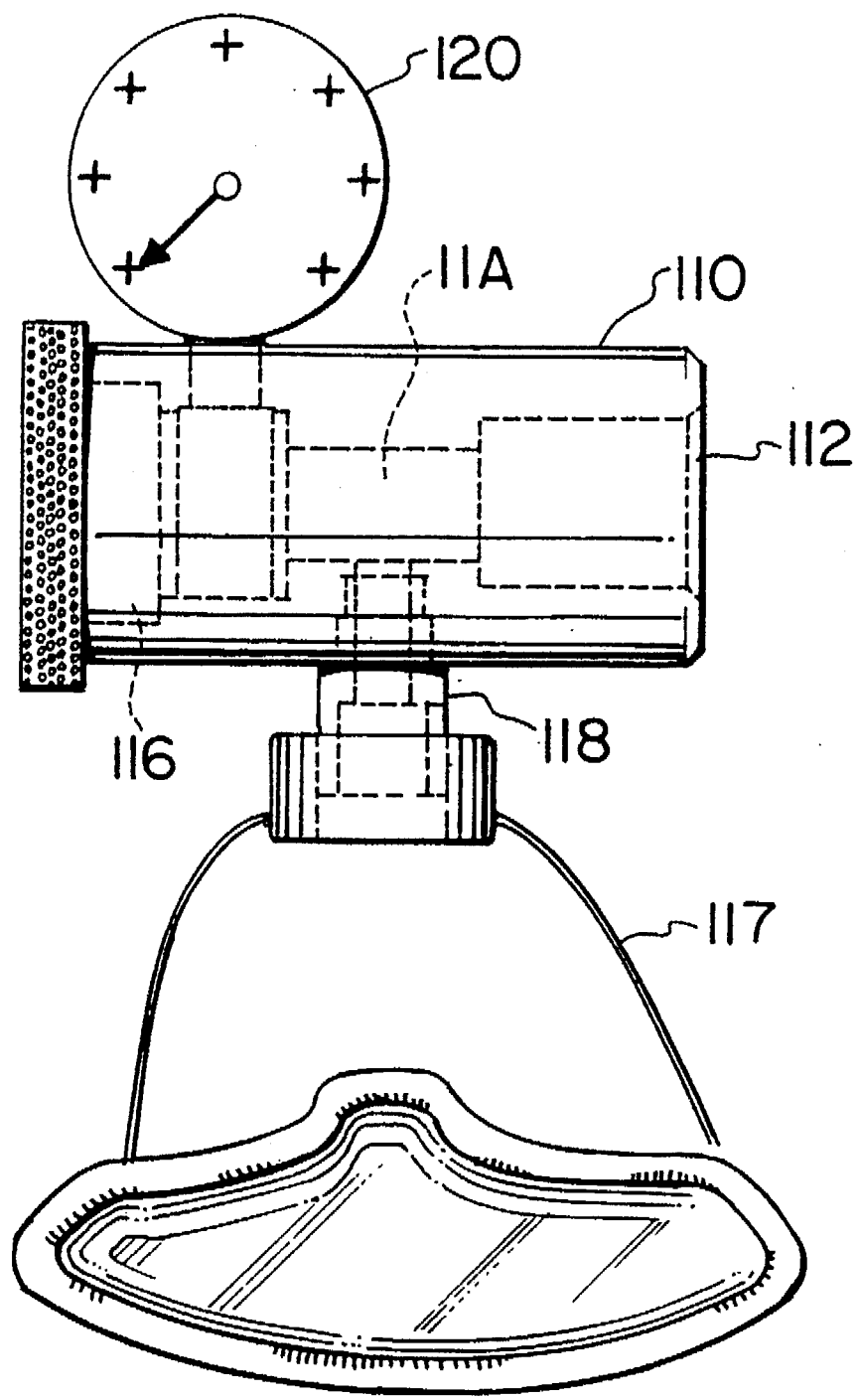
FIG. 8 illustrates a connector for providing a pressure relief valve.

FIG. 8 illustrates the addition of an auxiliary connector 110 which is attached at one end 112 to the outlet 10 of the control valve assembly. A through bore 114 contains a pressure relief valve 116. A face mask 117, or other form of gas delivery means, is connected to the bore 114 of the connector 110 at 118. A pressure gauge 120 can also be connected to the bore 114.

Figure 9:
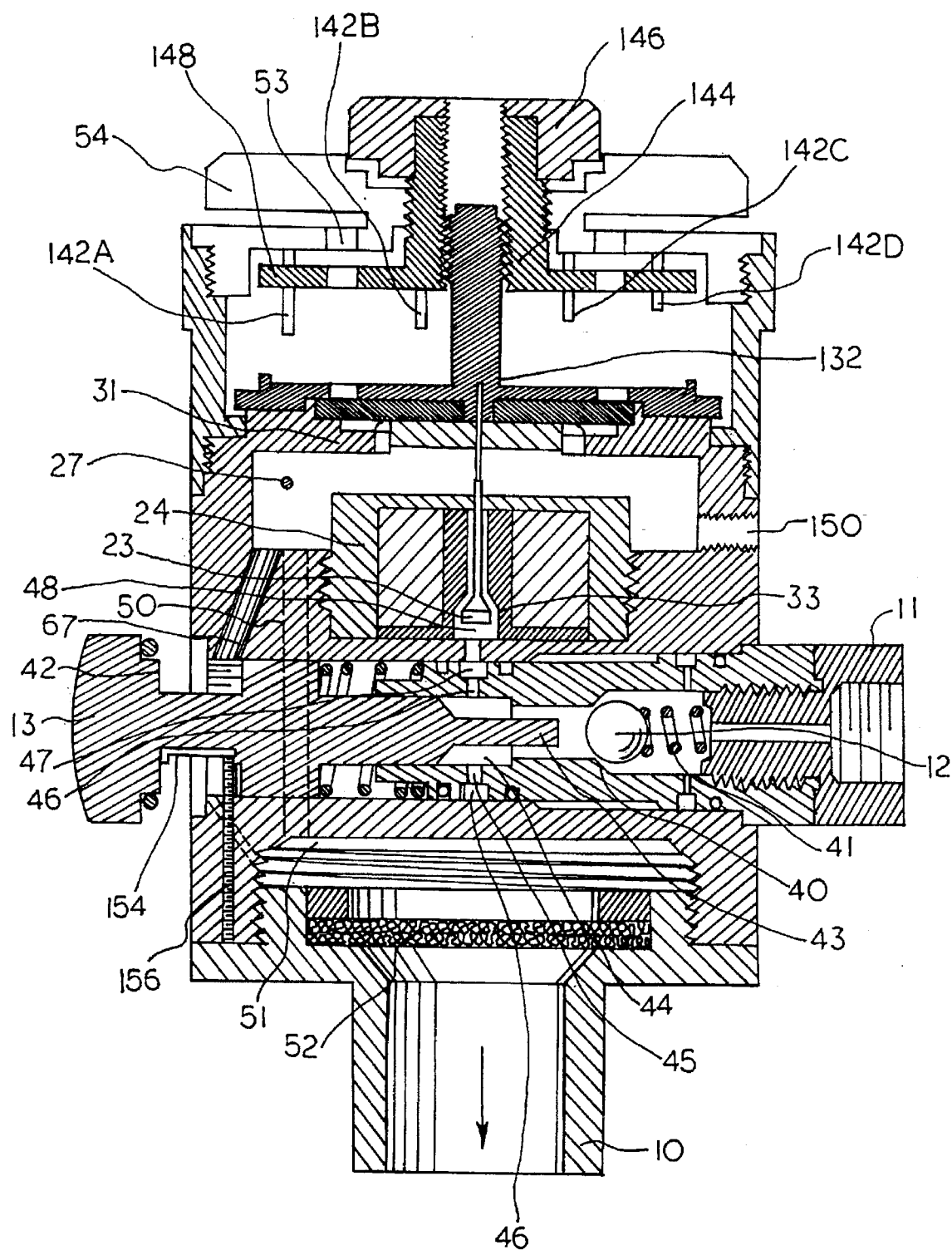
FIG. 9 is a vertical cross-section through the device according to a further embodiment of the present invention.
Figure 10:
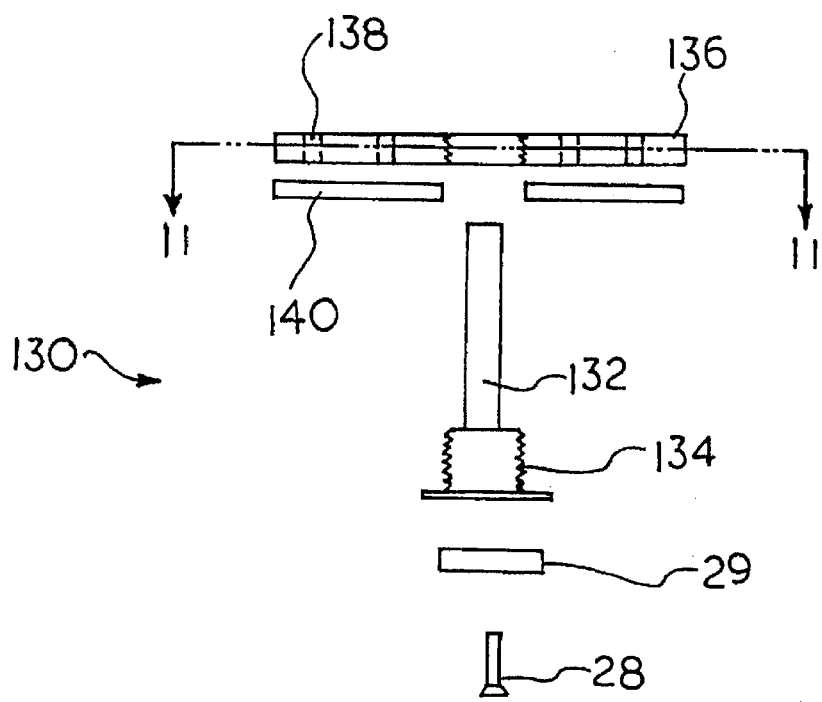
FIG. 10 is an exploded cross-sectional view of the main valve assembly of the embodiment of the apparatus shown in FIG. 9.
Figure 11:
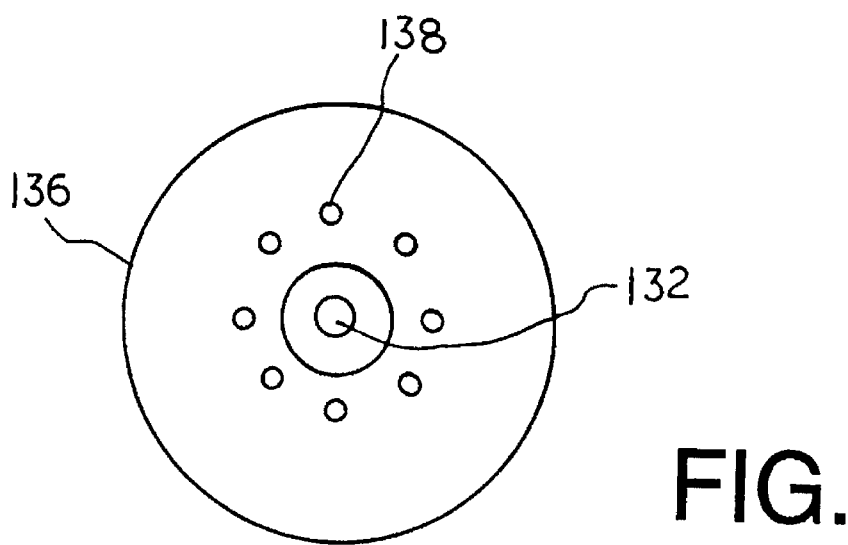
FIG. 11 is a sectional view along line 1111 in FIG. 10.

Referring now to FIGS. 9 through 11, shown is a further embodiment of the present invention. The main valve member, denoted by numeral 130, includes an elongate stem of 132 one end of which is threaded at 134. Bolt 28 holds magnetic member 29 in contact with the stem 132. Threads 134 on stem 132 are threadably received in valve head 136. By making use of the threaded stem and head arrangement, adjustment of the distance between the magnetic member 29 relative to the magnetic member 25 is possible. This is useful during assembly and calibration of the device.

As is illustrated in FIGS. 10 and 11, valve head 136 includes a plurality of apertures 138 extending therethrough and shown in the example to be in a coaxial relationship with valve head 136. The arrangement of the apertures 138 is only exemplary and it will be appreciated that any form and any number of apertures 138 may be provided for in valve head 136.

By making use of apertures 138 in valve 132, this feature facilitates the ingress of ambient air into the device and subsequently becoming available to the patient when there is a negative pressure generated within chamber 27 as would be the situation during spontaneous breathing or a patient breathing normally.

In order to prevent a lack of pressurization within chamber 27 during exhalation by passage of gas through apertures 138, a one-way flexible valve member 140 is disposed on the underside valve head 136 and flexible one-way valve member 140 covers the entire area of the apertures 138. As will be appreciated, during exhalation, the pressure of the exhaled gas from the patient forces the flexible one-way valve against the apertures 138 in valve head 136 and therefor blocks the passage of gas through these apertures. In this manner, adequate pressurization within chamber 27 can be achieved.

FIG. 9 illustrates the disposition of the main valve member 130 as positioned within the device. As a further attendant advantageous feature, the interior of a device and more particular the interior of the housing 20 includes a plurality of variable length and variable depth longitudinally disposed grooves 142A, 142B, 142C and 142D as illustrated in FIG. 9. As is illustrated, the length of groove 142A is greater than that of groove 142D. The grooves 142A through D have been found useful to effect control of the rate of flow of the exhaled gases from the device. Working in concert to effect the control of the exhaled gas, is an adjustable mechanical valve limiting member or stop member 144. Stop member 144 is threadably received within deflector 54 and includes an adjusting knob 146 which may be rotated to either advance the stop member 144 towards the head 132 of valve 130 or move the stop member 144 in a greater spaced relationship thereto. By making use of the adjustable stop member 144, the operator, by rotating adjustment knob 146 can vary the number of and degree of exposure of the grooves 142A through 142D. As is shown in the example in FIG. 9, all of the grooves 142 are exposed with the greatest amount of exposure being for groove 142A with the least at 142D. Although not shown, it will be readily appreciated that stop member 144 can be moved downwardly towards valve head 136 such that only a small portion of groove 142 is exposed. The periphery of stop member 144 include an O-ring 148 to ensure a positive seal of stop number 148 within chamber 27.

By varying the distance of the stop member 144 relative to the top of the valve head 136, it is clear that this reduces the internal volume therebetween. This, of course, has an effect on the expiration rate of gas through the device and accordingly, permits metering of the gases and therefor provides the possibility of adjusting the inspiratory to expiratory ratio.

As a further possible embodiment, the main housing 20 main be threaded and rotatable relative to the remaining portion of the body. In this instance, stop member 144 would remain fixed as opposed to being threaded and adjustable by adjustable knob 146. By simply rotating the housing 20, the degree of exposure of grooves 142A through D could be varied.

In operation, as the patient exhales and the gas reaches chamber 27 as set forth herein previously, valve head 136 is forced from its seating 31 and upwardly until it reaches stop member 144. At this time, the gas pressure is relieved by the gas travelling through at least one of the grooves 142A through D and subsequently upwardly vents 53, the gas being deflected by deflector 54.

During the inhalation process, valve number 130 is moved downwardly to move away from 136. In the process, as indicated briefly hereinabove, the provision of a flexible one-way valve and apertured valve head 136 permits the ingress of ambient air into chamber 27 via vents 53. As will be clear, there will be a pressured difference from one side of the valve head 136 to the other and accordingly, due to the slightly negative pressure difference relative to the top portion of the valve head 136, the one-way valve flap 140 will become deflected from its seated position normally against the underside of valve 136 and more particularly, covering apertures 138 and permit passage of the ambient air through apertures 138 subsequently chamber 27. The flow of the gas will then follow in accordance with the path as set forth here in previously with respect to the other embodiments.

A further desirable feature is to provide a port 150 in the housing 20 and particularly for contact within chamber 27. Port 150 is useful for purposes of connecting a manometer or other pressure sensing means to monitor the pressure within chamber 27. This is particularly useful since if pressure changes are desirable, the operator simply needs to adjust the disposition of the stop member in order to adjust the subsequent gas pressure within chamber 27.

Further still, in order to facilitate more friendly use of the apparatus, button 13 includes a cam groove 154 for releasable engagement with the set screw 156. In this manner, button 13 can be moved in the direction of the arrow shown in FIG. 9 to a locked or unlocked position. Although a cam groove or BNC type connection is shown, it will be appreciated that any suitable releasable locking arrangement can be provided.

Thus, the invention provides a device or apparatus which can be used for resuscitation or inhalation, as required. There is a safe control of the maximum pressure which can be applied to the lungs, regardless of the pressure of the oxygen supply. The apparatus cycles manually or automatically for resuscitation, or can be set for non-manual control for inhalation. Compared to many forms of apparatus previously used, the present apparatus is very quick to apply and is also very simple. This enables treatment to start very quickly, an important feature where a patient is not breathing or has no pulse. Some of the prior art examples assist in breathing but do not actually "breathe" for the patient, as does the present invention, with both a positive pressure feed and a release of free air pressure between cycles. Prior art examples requiring adjustments to increase and decrease pressures, and with gauges to watch, are not suitable for emergency situations. The present invention provides an apparatus which is light and portable, quickly applied and operates with safe pressures and releases, being simple to use and automatic in function.

It will be understood that various modifications can be made to the above-described embodiments without departing from the spirit or scope of the invention.

I claim:

1. A flow control valve apparatus, comprising
   a chamber;
   selective metering means in said chamber for selectively metering gas pressure in said chamber;
   an adjustable valve member reciprocally mounted in said chamber and acted upon by gas pressure in said chamber, said valve including a plurality of apertures one-way flexible member adjacent said apertures for permitting flow of gas through said apertures;
   a flow control valve, acted upon by said valve member to an open position;
   means for connecting a high pressure source to an inlet of said flow control valve;
   means for connecting a variable pressure volume to said chamber;
   means for selectively connecting a low pressure volume to said chamber;
   a first magnetic member on said valve member;
   a second magnetic member in spaced opposition to said first magnetic member;
   one of said first and second magnetic members being magnetized, to restrain movement of said valve member by said gas pressure in said chamber;
   said valve member being moved against restraint when said variable pressure reaches a predetermined maximum value, to permit closing of said flow control valve, and to permit said connection of said low pressure volume to said chamber; and
   said valve member being moved with restraint when said variable pressure reaches a predetermined low value to open said flow control valve.

2. A device as claimed in claim 1, wherein in said metering means comprises a plurality of grooves in said chamber, said grooves being in fluid communication with said interior of said chamber and exterior of said device, said metering means further including adjustable means for adjusting exposure of a gas in said chamber to said grooves.

3. A device as claimed in claim 2, wherein said adjustable means comprises an adjustable stop member for limiting reciprocal movement of said valve member.

4. A device as claimed in claim 2, wherein said plurality of grooves vary in length from one another.

5. A device as claimed in claim 4, wherein said plurality of grooves vary in depth.

6. A device as claimed in claim 1, wherein said adjustable valve includes a stem and a head, said head including said magnetic member and being adjustable relative to said stem for varying the distance between the magnetic members.

7. A device as claimed in claim 6, wherein said valve head includes said plurality of apertures therethrough and a one-way flexible valve adjacent said head.

8. A device as claimed in claim 7, wherein said one-way valve comprises a flexible flap valve.

9. A device as claimed in claim 1, wherein said means for connecting a high pressure source to an inlet of said flow control valve includes valve means and means for actuating said valve means to permit the flow of said high pressure source, said actuation means further including releasably engagable lock means for releasably locking said actuation means in an actuating position.

10. A device as claimed in claim 1, wherein said device further includes means for connecting a pressure monitoring means for monitoring the pressure in said chamber.

11. A device as claimed in claim 10, wherein said means for connecting a pressure monitoring means comprises a port, said port being in communication with said chamber.

12. In a resuscitation and inhalation apparatus including a chamber; a valve member reciprocally mounted in said chamber and acted upon by gas pressure in said chamber; a flow control valve acted upon by said valve member to an open position; means for connecting a gas volume to said apparatus, the improvement comprising:

metering means in said chamber for selectively metering gas pressure in said chamber.

13. The resuscitation and inhalation apparatus as set forth in claim 12, wherein said metering means comprises a plurality of grooves in said chamber, said grooves in fluid communication with said chamber and a point outside chamber, said metering means further including adjustable means for adjusting exposure of a gas in said chamber to said grooves.

14. A device as claimed in claim 13, wherein said grooves extend in varying lengths within said chamber, said adjustable means for adjusting exposure of a gas in said chamber to said grooves comprising an adjustable stop member for limiting the movement of said valve member within said chamber thereby upon movement of said valve member under positive pressure against said stop member, gas flow is past through said grooves.

15. A device as claimed in claim 12, wherein said valve member includes an apertured head and a movable one-way flexible flap valve for selectively covering said apertures.

16. A device as claimed in claim 15, wherein said one-way flap valve is movable from an aperture covering position under positive pressure and movable to a second non-covering position under negative pressure in said chamber whereby ambient air may be drawn in to said chamber from a point outside of said chamber.

* * * * *